United States Patent [19]
Bull et al.

[11] Patent Number: 5,843,763
[45] Date of Patent: *Dec. 1, 1998

[54] DEHALOGENATION OF ORGANOHALOGEN-CONTAINING COMPOUNDS

[75] Inventors: Alan Bull; David J. Hardman; Brian M. Stubbs; Paul J. Sallis, all of Kent, United Kingdom

[73] Assignee: Hercules Incorporated, Wilmington, Del.

[ * ] Notice: The term of this patent shall not extend beyond the expiration date of Pat. No. 5,470,742.

[21] Appl. No.: 487,705

[22] Filed: Jun. 7, 1995

Related U.S. Application Data

[63] Continuation of Ser. No. 243,492, May 16, 1994, Pat. No. 5,470,742, which is a continuation of Ser. No. 866,216, Apr. 9, 1992, abandoned, which is a continuation-in-part of Ser. No. 690,765, Apr. 24, 1991, abandoned.

[51] Int. Cl.$^6$ .................................................. C12S 13/00
[52] U.S. Cl. ..................... 435/262.5; 435/262; 435/813
[58] Field of Search ................................. 435/262, 262.5, 435/280, 13.1, 54.1, 822, 830, 843, 813; 528/480, 488, 489; 162/164.1, 164.3, 164.6, 166, 168.2, 168.4, 168.5

[56] References Cited

U.S. PATENT DOCUMENTS

| | | |
|---|---|---|
| 2,926,154 | 2/1960 | Keim . |
| 3,197,427 | 7/1965 | Schmalz . |
| 3,332,901 | 7/1967 | Keim . |
| 3,779,866 | 12/1973 | Azarowicz . |
| 3,891,589 | 6/1975 | Ray-Chaudhuri . |
| 4,240,935 | 12/1980 | Dumas . |
| 4,323,649 | 4/1982 | Higgins . |
| 4,447,541 | 5/1984 | Peterson . |
| 4,452,894 | 6/1984 | Olsen et al. . |
| 4,477,570 | 10/1984 | Colarnotolo et al. . |
| 4,490,471 | 12/1984 | Ghisalba et al. . |
| 4,493,895 | 1/1985 | Colarnotolo et al. . |
| 4,511,657 | 4/1985 | Colarnotolo et al. . |
| 4,535,061 | 8/1985 | Chakrabarty et al. . |
| 4,664,805 | 5/1987 | Focht . |
| 4,759,944 | 7/1988 | Fasi et al. ............................... 426/650 |
| 4,761,376 | 8/1988 | Kulpa et al. . |
| 4,803,166 | 2/1989 | Kulpa et al. . |
| 4,804,629 | 2/1989 | Roy . |
| 4,806,482 | 2/1989 | Horowitz . |
| 4,816,403 | 3/1989 | Roy . |
| 4,833,086 | 5/1989 | Horowitz . |
| 4,853,334 | 8/1989 | Vandenbergh et al. . |
| 4,857,586 | 8/1989 | Bachem et al. . |
| 4,906,732 | 3/1990 | Farrar et al. ............................ 435/262 |
| 4,925,802 | 5/1990 | Nelson et al. . |
| 4,959,315 | 9/1990 | Nelson et al. . |
| 4,968,427 | 11/1990 | Glamser et al. . |
| 4,975,499 | 12/1990 | Bachem et al. . |
| 5,019,606 | 5/1991 | Marten et al. . |
| 5,024,949 | 6/1991 | Hegeman et al. . |
| 5,110,740 | 5/1992 | Pokora et al. ......................... 435/262 |

FOREIGN PATENT DOCUMENTS

| | | |
|---|---|---|
| 258993 | 7/1987 | European Pat. Off. . |
| 257610 | 8/1987 | European Pat. Off. . |
| 258666 | 8/1987 | European Pat. Off. . |
| 0332967 | 9/1989 | European Pat. Off. . |
| 0349935 | 1/1990 | European Pat. Off. . |
| 0 393 916 | 10/1990 | European Pat. Off. . |
| 635048 | 11/1978 | U.S.S.R. . |
| 865727 | 4/1961 | United Kingdom . |
| 91/15520 | 10/1991 | WIPO . |

OTHER PUBLICATIONS

Kasai et al., "Degradation of 2,3–Dichloro–1–proppanol by a Pseudomonas sp.", *Agric. Biol. Chem.*, 54 (12) (1990), pp. 3185–3190.

Wijngaard et al., "Degradation of Epichlorohydrin and Halohydrins by Bacterial Cultures Isolated from Freshwater Sediment", *Journal of General Microbiology*, 135 (1989), pp. 2199–2208.

Wijngaard et al., "Purification and Characterization of Haloalcohol Dehalogenase from Arthrobacter sp. Strain AD2", *Journal of Bacteriology*, 173 (1991), pp. 124–129.

Janssen et al., "Purification and Characterization of a Bacterial Dehalogenase with Activity toward Halogenated Alkanes, Alcohols and Ethers", *Eur. J. Biochem.*, 171 (1988) pp. 67–72.

Castro et al., "Biological Cleavage of Carbon–Halogen Bonds Metabolism of 3–Bromopropanol by Pseudomonas sp.", *Biochimica et Biophysica Acta*, 100 (1965), pp. 384–392.

Ferguson et al., "Investigation of Anaerobic Removal and Degradation of Organic Chlorine from Kraft Bleaching Wastewaters", *Water Sci. Tech.*, 24, No. 3/4 (1991), pp. 241–250.

Janssen et al., "Hydrolytic and Oxidative Degradation of Chlorinated Aliphatic Compounds by Aerobic Microorganisms", *Advan. Appl. Biotechnol. Ser.* (1990), pp. 105–125.

Omori et al., "Bacterial Dehalogenation of Halogenated Alkanes and Fatty Acids", *Applied and Environmental Microbiology*, 35 No. 5 (1978), pp. 867–871.

Thayer, "Bioremediation: Innovative Technology for Cleaning Up Hazardous Waste", *Chemical and Engineering News* (Aug. 26, 1991), pp. 23–44.

Frick, "Microbiological Cleanup of Groundwater Contaminated by Pentachlorophenol", p. 1, Omenn, *Environmental Biotechnology*, Plenum Press (1988).

(List continued on next page.)

*Primary Examiner*—William H. Beisner
*Attorney, Agent, or Firm*—Greenblum & Bernstein P.L.C.

[57] ABSTRACT

Enzymatic dehalogenation of undesirable nitrogen-free organohalogen compounds is carried out by adding a dehalogenase to an aqueous composition comprising a nitrogen-free organohalogen compound and a nitrogen-containing cationic polymer. The enzymatic dehalogenation of the nitrogen-free organohalogen compound is achieved without any substantial effect upon the nitrogen-free organohalogen compound. The dehalogenation method may be carried out via continuous, batch, or semi-continuous processes.

84 Claims, No Drawings

OTHER PUBLICATIONS

Crawford et al., "Microbiological Removal of Pentachlorophenol from Soil Using a Flavobacterium", *Enzyme Microb. Technol.,* vol. 7 (Dec. 1985), p. 617.

"Biotrol Treatment Systems" brochure (date unknown), 4 pages.

EPA/540/5–88/003 (Nov. 1988), "The Superfund Innovative Technology Evaluation Program: Technology Profiles", pp. 13–16.

N. Dunlop–Jones, *Paper Chemistry,* Chapter 6: Wet–strength Chemistry, pp. 76–95, (1991).

M.H.J. Jacobs et al., Characterization of the epoxide hydrolase from an epichlorohydrin–degrading Pseudomonas sp., *European Journal of Biochemistry,* pp. 1–6 (Feb., 1991).

Hardman, D.J. and Slater, J.H. (1981) "Dehalogenases in Soil Bacteria", *J. Gen. Microbiol.,* 123, 117–128.

Jensen, H.L. (1960) "Decomposition of Chloroacetates and Chloropropionates by Bacteria", *Acta Agric. Scand.,* 10, 83–103.

Little, M. and Williams, P.A. (1971) "A Bacterial Halidohydrolase, Its Purification, Some Properties and Its Modification by Specific Amino Acid Reagents", *Eur. J. Biochem.,* 21, 99–109.

Senior, E. et al., (1976) "Enzyme Evolution in a Microbial Community Growing on the Herbicide Dalapon", *Nature,* 263, 476–479.

Tonomura, K. et al., (1965) "Defluorination of Monofluroacetate by Bacteria. Part I. Isolation of Bacteria and Their Activity of Defluorination", *Agric. Biol. Chem.,* 29, No. 2, pp. 124–128.

Slater, J.H. et al., (1979) "The Growth of *Pseudomnas putida* on Chlorinated Aliphatic Acids and Its Dehalogenase Activity", *J. Gen. Microbiol.,* 114, 125–136.

Weightman, A.J. et al., (1980) "Selection of *Pseudomanas putida* Strains with Elevated Dehalogenase Activities by Continuous Culture Growth on Chlorinated Alkanoic Acids", *J. Gen. Microbiol.,* 121, 187–193.

Sallis, et al., Isolation and Characterization for Haloalkane Haledolydralase from *Rhodococcus eltropolis* g2 J. Gen. Micro. v.136, pp. 115–120 (1990).

DEHALOGENATION OF ORGANOHALOGEN-CONTAINING COMPOUNDS

This application is a continuation of application Ser. No. 08/243,492, filed May 16, 1994, now U.S. Pat. No. 5,470, 742, which is a continuation of application Ser. No. 07/866, 216, filed Apr. 9, 1992, now abandoned, which is a continuation-in-part of application Ser. No. 07/690,765, filed Apr. 24, 1991, now abandoned, the disclosures of which are hereby incorporated in their entirety, by reference thereto.

BACKGROUND OF THE INVENTION

1. Field of the Invention

The present invention relates to reducing the levels of nitrogen-free organohalogen compounds in aqueous compositions. More particularly, the present invention relates to the purification of aqueous compositions comprising a nitrogen-free organohalogen compound and a nitrogen-containing cationic polymer. The invention also relates to a composition comprising a nitrogen-containing cationic polymer together with a nitrogen-free organohalogen compound and an enzyme. The invention further relates to a paper wet strengthening formulation, and to a paper product comprising a nitrogen-containing cationic polymer together with a residue of a microorganism. Finally, the present invention relates to continuous, catch, and semi-continuous methods for making the above-described aqueous composition, as well as to a papermaking method utilizing the composition of the present invention.

2. Background and Relevant Information

Aqueous polymer products made by methods involving haloalkylene oxide reactants often contain unwanted nitrogen-free organohalogen byproducts which are considered to be pollutants. For example, reactions involving epichlorohydrin, used as an intermediate in the manufacture of a wide variety of chemicals and polymers in aqueous media, can lead to the formation of 1,3-dichloro-2-propanol (DCP) and 1-chloro-2,3-propanediol (CPD). These unwanted byproducts are formed by the reaction of epichlorohydrin with evolved chloride ion and water. Increasing environmental concerns have created a demand for products that are free from such environmentally unsound byproducts as 1,3-dichloro-2-propanol and 1-chloro-2,3-propanediol, as well as unreacted epichlorohydrin and other halogenated oxyalkylene compounds.

Physical methods of decontaminating aqueous reaction products containing unwanted nitrogen-free organohalogen byproducts are known, such as solvent extraction with a water-immiscible solvent, or adsorption on a solid adsorbent, such as charcoal. However, such known methods can result in depletion of the reaction product, as well as requiring costly measures to recover and purify the solvent or adsorbent. Furthermore, such methods still leave the problem of how to ultimately dispose of the contaminants, i.e. the undesired halogenated oxyalkylene compounds.

It is known that nitrogen-free organohalogen-containing compounds can be converted to a relatively harmless substance. For example, 1,3-dichloro-2-propanol, 1-chloro-2,3-propanediol, and epichlorohydrin have been treated with alkali to produce glycerol.

The conversion of nitrogen-free organohalogen compounds with microorganisms containing a dehalogenase is also known. For example, C. E. Castro, et al. ("Biological Cleavage of Carbon-Halogen Bonds Metabolism of 3-Bromopropanol by *Pseudomonas sp.*", *Biochimica et Biophysica Acta*, 100, 384–392, 1965) describe the use of *Pseudomonas sp.* isolated from soil that metabolizes 3-bromopropanol in sequence to 3-bromopropionic acid, 3-hydroxypropionic acid and $CO_2$.

Various U.S. Patents also describe the use of microorganisms for dehalogenating halohydrins, e.g. U.S. Pat. Nos. 4,452,894; 4,477,570; and 4,493,895.

Finally, commercial papermaking operations utilize paper wet strengthening formulations which comprise nitrogen-containing cationic polymers as well as nitrogen-free organohalogen compounds. In the papermaking process, waste material is frequently disposed of in landfills, etc. This waste is a substantially solid mass of material which is exposed to the environment. The exposure of the waste to the environment results in the selection of microorganisms which feed on the components in the waste. It is knowm that there are microorganisms which feed on the nitrogen-free organohalogen compounds in the solid waste.

SUMMARY OF THE INVENTION

The present invention is directed to the enzymatic dehalogenation of halogenated nitrogen-free organic compounds, in order to produce polymeric products in usable form.

For some time it has been known that there are certain microorganisms which contain an enzyme capable of dehalogenating nitrogen-free organohalogen compounds. These microorganisms dehalogenate environmentally-damaging organohalogen compounds. However, these microorganisms have not been utilized in commercial papermaking operations. Rather, discarded organohalogen waste materials have been dehalogenated by these microorganisms, which exist freely in the environment.

The present invention involves a discovery of a means for utilizing the dehalogenating ability of certain enzymes in commercial operations carried out to produce compositions which are in "usable form", i.e. are not contaminated with soil. It has been unexpectedly discovered that nitrogen-containing cationic polymers are left substantially intact during enzymatic dehalogenation of nitrogen-free organohalogen compounds. This result is surprising because cationic polymers are adversely affected by other conditions used to produce dehalogenation. For example polyamides, and indeed all amides, are attacked by strong aqueous alkali to produce an amine and the carboxylic acid from which the amide was made. The result is also surprising because the microorganisms are found not to have any substantial undesirable effect upon the cationic polymer.

It has also been unexpectedly discovered that certain microorganisms are capable of dehalogenating nitrogen-free organohalogen compounds which are present at relatively high concentrations, such as in a reaction product from the polymerization of reactants which produce an epichlorohydrin resin. Surprisingly, such microorganisms are able to dehalogenate nitrogen-free organohalogen compounds present in such reaction products, without the nitrogen-free organohalogen compounds killing the microorganisms, especially when such reaction products are present at a concentration useful as a paper wet strengthening formulation.

For example, cationic polymers bearing 3-hydroxy azetidinium groups are important examples of polymers purified by the method of the present invention. The cationic 3-hydroxy azetidinium chloride group is reactive with alkaline solutions which convert the cationic groups to uncharged groups, as follows:

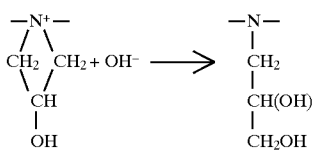

This reaction is undesired because the conversion of positively charged cationic polymer groups to uncharged polymer groups reduces the ability of the polymer to impart wet strength to paper. This undesired reaction reduces the performance of the polymer because the positively charged polymer (i.e. cationically charged) is attracted to negatively (i.e. anionically) charged paper fibers. The reaction above decreases the positive charge on the cationic polymer, and thereby impairs the bonding of the polymer to cellulose fiber.

Accordingly, a surprising result of the present invention is the discovery of a method for the dehalogenation of pollutant materials without sacrificing the nitrogen-containing cationic polymers which are present during the dehalogenation phase.

The present invention involves a method for treating an aqueous composition comprising a nitrogen-containing cationic polymer and a nitrogen-free organohalogen compound. The method comprises the steps of (1) adding an enzyme to the aqueous composition, and (2) dehalogenating the nitrogen-free organohalogen compound. A composition comprising a nitrogen-containing cationic polymer, a nitrogen-free organohalogen compound, and a dehalogenase enzyme, is also encompassed by the present invention.

The enzyme is preferably obtained from a microorganism, i.e. contained in a cell. Specific microorganisms which contain a dehalogenase include one or more members selected from the group consisting of a Coryneform organism 1, an Agrobacterium biovar I, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

These microorganisms are most effective when enriched and isolated, followed by being cultured to a high concentration. Accordingly, the present invention further relates to a method of enrichment and isolation of dehalogenase-containing microorganisms, followed by culturing the isolated microorganism to increase the population of the microorganism to a level effective to dehalogenate nitrogen-free organohalogen compounds present in a polymerization reaction product. The step of enrichment and isolation of a dehalogenase-containing microorganism is carried out by: (A) adding an environmental sample containing mixed microbial populations to a nitrogen-containing polymer and a nitrogen-free organohalogen compound; (B) incubating the mixture in either batch mode (preferably in a plurality of subculturing steps) or in continuous mode (i.e. by continuously supplying nitrogen-containing polymer and nitrogen-free organohalogen compounds, and continuously removing the effluent); and (C) isolating (i.e. selecting) specific microorganisms which contain one or more dehalogenases from the enrichment culture, on the basis of their ability to utilize nitrogen-free organohalogen compounds for growth. The incubation of the microorganism is preferably carried out by performing from 2 to 5 subculturing steps involving the addition of increasing concentrations of nitrogen-free organohalogen compound. The enriched and isolated microorganisms are then cultured to a concentration of at least $5 \times 10^7$ cells per milliliter, using a nitrogen-free organohalogen compound as a nutrient source.

The most preferred use of the compositions of the present invention is in the papermaking industry. The present invention provides a composition suitable for use as a paper wet strengthening formulation. The formulation comprises water, a nitrogen-containing cationic polymer, and preferably less than about 2.6 weight percent of a nitrogen-free organohalogen compound, based on the weight of the composition.

The present invention also encompasses a paper product comprising a nitrogen-containing cationic polymer and a residue of a microorganism. The phrase "paper product" includes all sheet and web materials formed by the deposition of vegetable, mineral, animal, or synthetic fibers, or their mixtures, especially cellulosic fibers. The "residue of the microorganism" in the paper product is that portion of a dehalogenase-containing microorganism which remains in the dry paper product after the completion of the papermaking process. The paper product generally comprises the microorganism residue in an amount up to about 100 grams, and more specifically an amount of from about 2.5 grams to about 100 grams of microorganism residue, per ton of paper product.

The present invention also relates to batch, continuous, and semi-continuous methods for making the composition of the present invention. Several important parameters in each of these methods include: (1) the type and concentration of the polymer, (2) the type and concentration of the organohalogen compound, and (3) the type and concentration of the biocatalyst.

The continuous method involves the steps of: (i) continuously feeding the stream of the aqueous composition into the reactor, and (ii) continuously removing the treated product from the reactor. Of course, flow rates and residence times are also of importance in successfully carrying out the continuous method.

The method of the invention may also be carried out in intermittent fashion, in which event the method is termed a "semi-continuous" method. In the semi-continuous method, the reactor may be run, for example, for an 8 to 16 hour period, followed by being operated batchwise for the remainder of the day. The semi-continuous method involves the criticalities of both the continuous method and the batch method.

Since the present invention is especially useful far the production of a paper wet strengthening formulation, the present invention further encompasses a method of making paper. The method comprises the steps of: (1) providing an aqueous composition comprising a nitrogen-containing cationic polymer and a nitrogen-free organohalogen compound; (2) adding an enzyme to the aqueous composition; (3) dehalogenating the nitrogen-free organohalogen compound, whereby a treated composition is produced; (4) using the treated composition to make a paper wet strengthening formulation; and (5) adding the paper wet strengthening formulation to a stream in a papermaking process. The enzyme is capable of dehalogenating the nitrogen-free organohalogen compound while leaving the nitrogen-containing polymer substantially intact.

Accordingly, it is an object of the present invention to reduce environmental pollution by dehalogenating nitrogen-free organohalogen compounds, especially organohalogen compounds produced in association with the production of nitrogen-containing cationic polymers. As a result, a further object of the present invention is to provide a method for making a paper wet strengthening formulation, as well as a method of making paper using the paper wet strengthening formulation of the present invention.

Finally, it is an object of the present invention to provide a paper wet strengthening formulation, as well as a paper product, both of which are substantially free of nitrogen-free organohalogen compounds.

DETAILED DESCRIPTION OF THE INVENTION

The present invention relates to methods for treating an aqueous composition comprising a nitrogen-containing cationic polymer and a nitrogen-free organohalogen compound. A major field of application for nitrogen-containing cationic polymers is in the manufacture of paper products, more specifically, wet strengthening formulations used in the production of paper.

A preferred group of polymers for use in the present invention includes cationic polymers, alone or together with other polymers used for the purpose of imparting wet strength to paper. A listing of many polymers useful in papermaking wet strengthening formulation is described in *Paper Chemistry*, ISBN 0-216-92909-1, pages 78–96, published in the USA by Chapman Hall, New York. Chapter 6 of this book is entitled "Wet Strength Chemistry", and is hereby incorporated, in its entirety, by reference thereto. Chapter 6 describes several classes of polymers which are used to impart wet strength to paper, including; polyaminoamide-epichlorohydrin resin, urea-formaldehyde resin, melamine-formaldehyde resin, epoxidized polyamide resin, glyoxalated polyacrylamide resin, polyethyleneimine resin, dialdehyde starch, proteinaceous adhesive treated with formaldehyde, cellulose xanthate (viscose), synthetic latex, vegetable gum, and glyoxal. The polyaminoamide-epichlorohydrin resin may be a Kymene® brand polyaminoamide-epichlorohydrin resin, such as Kymene® 557, Kymene® 2064, Kymene® 450, and Kymene® 367 resins.

The invention is directed to cationic polymers such as polyamino epichlorohydrin resins and polyaminoamide-epichlorohydrin resins, which may be used alone or in combination with the other polymers used for the wet strengthening of paper. These resins include epichlorohydrin resins and nitrogen-containing cationic polymers, both of which are derived from epichlorohydrin reactants. Preferred resins for the purposes of this invention include polyaminoamide-epichlorohydrin wet-strength resins as described in U.S. Pat. Nos.: 2,926,154; 3,332,901; 3,891,589; 3,197,427; 4,240,935, 4,857,586; European Patent Publication 0,349,935, and Great Britain Patent 865,727. Processes for making these known resins are also disclosed in these documents, which are incorporated in their entireties, by reference thereto.

Exemplary epichlorohydrin resins in these patents are characterized by the presence of N-chlorohydrin groups of the formula:

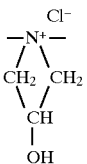

and isomeric 3-hydroxyazetidinium chloride groups of the formula:

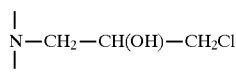

A preferred cationic polymer utilized in the present invention is a polymer having the following formula:

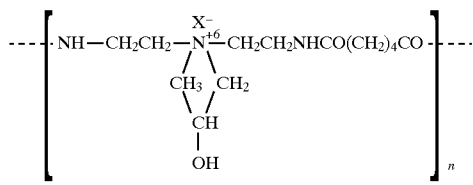

where the asterisked tetrasubstituted nitrogen atom is positively charged (a quaternary nitrogen), and hence cationic. The nitrogen atom is in a 4-membered ring (i.e. a 3-hydroxyazetidinium group). Other uncharged polymer units also co-exist along polymer chains of this type of resin. Even though a few negatively charged (i.e. anionic) groups may also be present on the polymer, the net charge along the polymer chain is positive. X⁻ is a simple anion which is not covalently bonded to the polymer chain. Generally the anion is a chloride ion, and n is an integer of from 5 to several thousand.

The examples set forth below involve the treatment of a class of polymers comprising both a polymeric backbone and ionic 3-hydroxy azetidinium chloride groups.

The polymeric reaction. product (i.e. the nitrogen containing cationic polymer) is generally present in the aqueous composition being treated at a level of at least about 1 weight percent, preferably at a level of at least about 5 weight percent, and still more preferably at a level of at least about 10 weight percent, based on the total weight of the aqueous composition.

In the composition of the present invention, the nitrogen-containing cationic polymer is preferably present in an amount of from about 1 to 50 weight percent, preferably at a level of from about 5 to 35 weight percent, and most preferably at a level of from about 10 to 25 weight percent, based on the total weight of the composition.

The composition of the present invention may be used, by itself, as a paper wet strengthening formulation. The composition may also be used in conjunction with additional polymers, which are preferably mixed into the composition, for subsequent use as a paper wet strengthening agent.

Nitrogen-free organohalogen compounds which may be treated according to the invention comprise unreacted reactants as well as reaction byproducts of the processes for making the above-described polyaminoamide-epichlorohydrin polymers. These nitrogen-free organohalogen compounds include, for example, dihaloalkanols having the formula:

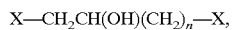
X—CH₂CH(OH)(CH₂)ₙ—X, and haloalkanediols having the formula

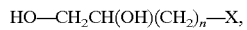
HO—CH₂CH(OH)(CH₂)ₙ—X, where n is generally an integer of from 1 to 4 (inclusive), particularly where n is 1, and X is a halogen atom such as chlorine, bromine, or iodine, particularly where X is chlorine. Generally the nitrogen-free organohalogen compounds are monohaloalkanediols and dihaloalkanols. Examples of dihaloalkanols include 1,3-dichloro-2-propanol and 1,4-dichloro-2-butanol. Examples of haloalkanediols include 1-chloro-2,3-butanedial and 1-chloro-3,4-propanediol. Other contaminants that can be dehalogenated in accordance with the present invention will be readily apparent to the skilled artisan.

In the production of typical commercial synthetic water-soluble epichlorohydrin resins, such as a polyaminoamide-epichlorohydrin wet-strength resin, there is generally present at least one member selected from the group consisting of a nitrogen-free, non-polymeric, halogen-containing alcohol, and a nitrogen-free haloalkylene oxide. The undesired organohalogen byproduct which is produced is generally at least one member selected from the group consisting of a nitrogen-free, nonpolymeric, halogen-containing alcohol, and a nitrogen-free haloalkylene oxide. Polymeric reaction products often comprise 1,3-dichloro-2-propanol, and 1-chloro-2,3-propanediol, both of which are byproducts from the reaction of epichlorohydrin with a polyaminoamide resin.

Before dehalogenation, the amount of nitrogen-free organohalogen contaminants in aqueous solutions generally is from about 0.1 to 25 weight percent, based on the weight of the aqueous composition. Preferably the nitrogen-free organohalogen compounds are present in an amount of from about 0.2 to 12 weight percent, still more preferably from about 0.3 to 8 weight percent. Since the final concentration of the nitrogen-free organohalogen compounds can be as low as about 0.1 parts per million, the full range of the concentration of the nitrogen-free organohalogen compounds is from about 0.1 parts per million to about 25 weight percent, based on the weight of the composition. Preferably, the concentration of the nitrogen-free organohalogen compound is from about 0.1 parts per million to about 2.6 weight percent, based on the weight of the composition.

In accordance with the present invention, haloalkylene oxides are compounds of the formula:

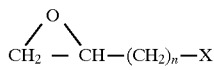

wherein X is a halogen atom such as chlorine, bromine, or iodine, and where n is an-integer of from 1 to 4. Preferably X is chlorine. Preferably n is 1. Specific haloalkylene oxides frequently present in the reaction product mixture include 1-chloro-2,3-epoxypropane (i.e. unreacted epichlorohydrin), 1-bromo-2,3-epoxypropane, and 1-chloro-3,4-epoxybutane. One of the most troublesome nitrogen-free haloalkylene oxide compounds is unreacted epichlorohydrin.

In the production of the above-described nitrogen-containing cationic polymers, nitrogen-free organohalogen compounds include both remaining reactants (e.g. epichlorohydrin) as well as unwanted byproducts, such as the halogenated alcohols described above. Since organohalogen compounds are considered to be pollutants, it is preferable that they are converted to an environmentally harmless form.

The present invention involves the reaction of an enzyme with the nitrogen-free organohalogen compound, whereby the nitrogen-free organohalogen is dehalogenated. As used herein, the term "enzyme" refers to any-dehalogenase, i.e. any enzyme capable of dehalogenating a nitrogen-free organohalogen compound. Preferably the enzyme is a "biocatalyst", i.e. an enzyme obtained from a living cell, which is thereafter used for the dehalogenation of nitrogen-free organohalogen compounds.

The biocatalyst may be provided in the form of either living cells or as an immobilized, unrefined cell-free extract or refined dehalogenase. The term "biodehalogenation" refers to the dehalogenation of a nitrogen-free organohalogen compound using a biocatalyst.

As the microorganism capable of biodehalogenation of the nitrogen-free organohalogen-containing compound in accordance with the present invention, there is contemplated any microorganism that is capable of achieving a high degree of dehalogenation of the nitrogen free organohalogen compounds described above, in the presence of the nitrogen-containing cationic polymer, while leaving the nitrogen-containing cationic polymer intact. The concentration of the microorganism in the composition of the present invention is preferably at least $5 \times 10^7$ cells per milliliter, more preferably at least $10^8$ cells per milliliter, and most preferably at least $10^9$ cells per milliliter. Preferably, the microorganism (or mixture of microorganisms) is of a type which dehalogenates the nitrogen-free organohalogen compounds even when the microorganism is present in an amount of less than one percent by weight vis a vis the remainder of the aqueous product, that is, less than one percent based on the weight of the aqueous solution of a polyaminoamide-epichlorohydrin wet strength resin.

Such microorganisms are obtainable by batch enrichment culture. Inoculation of enrichment isolation media with soil samples taken from organohalogen-contaminated soil results in mixed microbial communities, which can be sub-cultured, in a plurality of subculturing steps (preferably 2 to 5 subculturing steps), using increasing concentrations of the particular organohalogen-containing compound for which selection is sought.

Dehalogenating the nitrogen-free organohalogen compounds in a continuous process is preferably carried out using the nitrogen-free organohalogen compound as the growth-limiting nutrient. The temperature and pH are preferably controlled in order to maximize the effectiveness of microorganisms. A temperature of about 30° C. and a pH of about 5.8 have been found to be preferred conditions for continuous dehalogenation. It is also preferred to agitate the culture vessel, preferably with an agitation rate of about 350 rpm.

During a process in which a continuous culture of microorganisms dehalogenates nitrogen-free organohalogen compounds, the pH is preferably lowered as processing continues, because the hydroxyl ion is abstracted from water and the hydrogen ion concentration in water is simultaneously increased. Thus, during the process the pH is lowered from, for example, about 6.5 to about 2.8. During this time it is also preferable to increase the flow rate of the aqueous composition being fed into the culture medium, to decrease the residence time of the product stream in the reactor. Thus, during the process the flow rate may, for example, be increased from a rate of about 0.1 liter per hour, to a rate of 0.18 liters per hour.

A preferable community is one that releases 100% of the organochlorine from 1,3-dichloro-2-propanol into the medium as inorganic chlorine in batch cultures containing 26 grams per liter of 1,3-dichloro-2-propanol, more preferably 0.950 grams per liter of 1,3-dichloro-2-propanol, most preferably 0.0000625 grams per liter of 1,3-dichloro-2-propanol. Another preferable community is one that releases 26 grams per liter of 1-chloro-2,3-propanediol into the medium as inorganic chlorine, more preferably 0.950 grams per liter of 1-chloro- 2,3-propanediol, most preferably 0.005 grams per liter of 1-chloro-2,3-propanediol.

In the dehalogenation of 1,3-dichloro-2-propanol and 1-chloro-2,3-propanediol in accordance with the present invention, that is, converting covalently bonded chlorine to chloride ion, the microorganism preferably dehalogenates the nitrogen-free organohalogen-containing compound until the aqueous mixture (wet basis, 12.5% solids based on non-volatile matter) has less than about 26,000 parts per million 1-chloro-2,3-propanediol and 26,000 parts per million 1,3-dichloro-2-propanol. Based on the dry weight of synthetic water-soluble epichlorohydrin-polyaminoamide resin, dehalogenation proceeds to less than about 208,000 parts per million 1-chloro-2,3-propanediol and 208,000 parts per million 1,3-dichloro-2-propanol. More preferably, the amount of the nitrogen-free, non-polymeric, halogen-containing alcohols (e.g. 1-chloro-2,3-propanediol and 1,3-dichloro-2-propanol) is reduced to less than about 950 parts per million on a wet basis (7,600 parts per million dry basis). Still more preferably, the amount of the nitrogen-free, non-polymeric, halogen containing alcohols is reduced to about 5 parts per million on a wet basis (40 parts per million dry basis). The microorganisms capable of achieving these degrees of dehalogenation of the nitrogen-free organohalogen compounds are considered to be preferred microorganisms in the practice of the present invention.

Exemplary microorganisms include (1) Coryneform organism 1 (NCIMB 40271, *Arthrobacter erithii*), (2) *Agrobacterium biovar* I (NCIMB 40272, *Agrobacterium tumefaciens*), (3) *Pseudomonas cepacia* (NCIMB 40273, *Pseudomonas cepacia*), (4) *Arthrobacter histidinolovorans* HK1 (NCIMB 40274), (5) *Agrobacterium biovar* III, (6) Coryneform organism 2 (NCIMB 40383, *Rhodoccocus dehalogenans*), and (7) *Agrobacterium tumefaciens* HK7 (NCIMB 40313). NCIMB 40271, 40272, 40273 and 40274 were deposited on Apr. 4, 1990. NCIMB 40313 was deposited on Aug. 31, 1990 and NCIMB 40383 was deposited on Mar. 11, 1991. Enzymes (dehalogenases) obtained from these microorganisms as well as cell-free extracts therefrom are also useful in accordance with the present invention, as it is the enzymes (i.e., dehalogenases) which are the active ingredients within the microorganisms.

The most preferred biocatalyst for use in the method of the present invention is a two-component mixture of *Agrobacterium tumefaciens* and *Arthrobacter histidinolovorans*. Although the precise identity of the enzymes which make the method operable has not been made, it is believed that the enzymes which effectuate the method belong to the class of enzymes termed "hydrogen halide lyase type dehalogenase".

Alternatively, the microorganism or cell-free extract can be attached in film form on a suitable support material according to well known techniques, and then the aqueous mixture poured over the film. If a microorganism is present, nutrients, such as oxygen, nitrogen, and phosphorus, can be added to the aqueous composition, in sufficient quantities to maintain or promote the biodehalogenation process. In the case of the cell-free extract, the extract may also be held or entrapped within a suitable support, which must be capable of permitting the transport of the organohalogen contaminant.

The temperature range for performing the method of the present invention is preferably from about 10° C. to about 50° C., more preferably from about 15° C. to about 40° C., and most preferably from about 25° C. to about 36° C.

The method of the present invention is preferably performed at a pH of from about 3 to about 10. The pH can be maintained by the use of suitable pH buffers. When using cell-free extracts containing a dehalogenase, the pH is most preferably from about 7 to about 8. When using one or more microorganisms in accord with the present invention, the pH is more preferably from about 4 to about 8, and most preferably the pH is from about 5 to about 8. Dehalogenation proceeds at neutral or near neutral pH, with both the upper (alkali) limit and lower (acid) limits determined by the biocatalyst or the product.

The viscosity of the aqueous mixture can have an effect on the physical handling characteristics in the method of the present invention. Accordingly, a preferred practical upper viscosity limit is about 1000 mPa.s. Preferably the viscosity is less than about 250 mPa.s, and most preferably the viscosity is less than about 100 mPa.s. The lower viscosity limit is determined by the type and molecular weight of the product in the aqueous composition.

If desired, the microorganism or enzyme can be neutralized (i.e. killed) once a treated product is produced. Neutralization of the microorganism can be performed by reducing the pH of the aqueous mixture to 2.8, then adding a proprietary biocidal agent (e.g. Proxell® BD biocidal agent), which comprises potassium sorbate and 1,2-benzisothiazolin-3-one in sufficient quantity, normally 0.02% and 0.04% respectively, based on the weight of the aqueous composition.

The microorganism can be removed from the aqueous composition after dehalogenation. The removal may be performed by one or more of the steps of filtration, centrifugation, sedimentation, or any other known techniques for removing microbes from a mixture. The microorganisms mineralize the nitrogen free organohalogen compounds so producing $CO_2$, water, and biomass, with no glycerol left in the resin. Where the biocatalyst is an immobilized dehalogenase, the product of the reaction is glycidol.

A problem associated with the removal of the microbes from the mixture is that intensive methods of separation such as microfiltration remove not only microbes but also particles of cationic polymer, with the result that the wet strength properties are reduced, which is undesirable. Therefore it is preferable to leave the deactivated microorganism in the mixture to avoid the problem of reducing wet strength properties.

In general, the enzyme may be added to the composition in an amount of from about $2.5 \times 10^{-6}$ to $1 \times 10^{-4}$ weight percent, based on the weight of the composition. However, the enzyme is preferably added to the composition in an amount of from about $2.5 \times 10^{-5}$ to $0.75 \times 10^{-4}$ weight percent, most preferably in an amount of from about $4 \times 10^{-5}$ to $6 \times 10^{-5}$ weight percent, based on the weight of the composition.

The method of the resent invention may be a continuous method, a batch method, or a semi-continuous method.

The continuous method involves continuously feeding a stream of an aqueous composition to a reactor, and continuously contacting the stream of the aqueous composition with the biocatalyst whereby a treated product is formed, followed by continuously removing the treated product from the reactor. The contact between the aqueous biocatalyst and the nitrogen-free organohalogen compounds results in the dehalogenation and mineralization of the organohalogen compounds.

During the continuous method, the nitrogen-containing cationic polymer preferably has a residence time in the reactor of from about 6.5 hours to about 15 hours. A preferred steady-state concentration of the nitrogen-free organohalogen compound in the reactor is from about 0.1 part per million to about 500 parts per million, based on the weight of the treated product.

The batchwise method involves adding a batch of the aqueous composition to the reactor, followed by contacting the aqueous composition with the enzyme, followed by removing a batch of treated product from the reactor. During the batchwise method, the initial concentration of the nitrogen-free organohalogen compound is preferably less than about 2.6 weight percent. The final concentration of the nitrogen-free organohalogen compound is preferably from about 0.1 to 500 parts per million, on a weight basis. The enzyme is preferably present in the form of a microorganism, which is preferably present in the reactor at a level of at least $5 \times 10^7$ cells per milliliter. Although the batch method can in general be carried out by placing the microorganism in contact with the nitrogen-free organohalogen compound for a period of from about 2 hours to about 56 hours, preferably the batch method is carried out by placing the microorganism in contact with the nitrogen-free organohalogen compound for a period of from about 17 hours to about 22 hours.

The semi-continuous method can be carried out by continuously feeding a stream of an aqueous composition to a reactor during a period of continuous operation, and continuously contacting the stream of the aqueous composition with the enzyme, and continuously removing the treated product from the reactor, and periodically discontinuing the steps of:

i. feeding the stream of the aqueous composition into the reactor, and ii. removing the treated product from the reactor, wherein the periodic discontinuance of both of these steps is followed by a period of continuous operation of both steps.

In an alternative semi-continuous method, upon termination of the period of continuous operation, there is a partial drain down of the reactor, following which the feed stream is continued at the same or a reduced rate as during the period of continuous operation, but the removal of treated product does not occur until the end of the discontinuous period, generally from about 2 to 56 hours, preferably from about 8 hours (overnight) to 56 hours (i.e. over a weekend). The continuation of the feed stream prevents a subsequent failure of the reactor when the flow is restarted.

The semi-continuous method permits a resin making facility to operate the continuous method during daily production operations, while permitting a batch treatment of the aqueous composition to be discontinued during periods in which continuous paper productivity is temporarily suspended, e.g. overnight periods during which the operation of the papermaking facilities are temporarily halted. During the suspension of the continuous input of the aqueous composition stream into the reactor (along with suspension of the continuous removal step), a batch treatment may he performed on the composition which is in the reactor during the period of suspension of the continuous input and removal. In addition to the processes described above, the present invention pertains to compositions and a paper wet strengthening formulation produced according to the invention. The composition comprises a nitrogen-containing cationic polymer, a nitrogen-free organohalogen compound, and an enzyme capable of dehalogenating the nitrogen-free organohalogen compound, while leaving the polymer substantially intact. The composition preferably comprises one of the preferred resins described above, and preferably the enzyme is present in the form of a biocatalyst (most preferably, in microorganism) present in the concentrations described above.

The paper wet strengthening formulation of the present invention comprises water, a nitrogen-containing cationic polymer, and a nitrogen-free organohalogen compound. Preferably, the total amount of nitrogen-free organohalogen compounds present in the formulation comprise from about 0.1 to 10 parts per million, based on the weight of the composition. However, the nitrogen-free organohalogen compound is more preferably present in an amount of from about 0.1 to 5 parts per million, most preferably from about 0.1 to 2 parts per million. The paper wet strengthening formulation may further comprise an enzyme, in the event that the enzyme is not removed from the formulation after the dehalogenation reaction. Preferably, the paper wet strengthening formulation comprises the preferred polymers described above, in the preferred amounts described above.

The paper product of the present invention comprises paper, a nitrogen-containing cationic polymer, and a residue of a microorganism. The residue of the microorganism is present in an amount up to about 100 grams, and more specifically from about 2.5 grams to 100 grams, per ton of dry paper product. Preferably the paper product comprises a nitrogen-free organohalogen compound in an amount of less than about 0.1 parts per million, on a dry weight basis. The paper product preferably comprises at least one of the preferred polymers described above. The polymer is preferably present in the paper product in an amount of from about 0.1 to 5 weight percent, based on the weight of the dry paper product.

The invention is illustrated by the following Examples, which are provided for the purpose of representation, and are not to be construed as limiting the scope of the invention. Unless stated otherwise, all percentages, parts, etc., are by weight.

EXAMPLE 1

A polyaminoamide-epichlorohydrin resin is prepared as follows. A stirred mixture of 200 parts by weight diethylenetriamine and 290 parts by weight adipic acid is heated to 170° C. to 175° C. for 190 minutes with evolution of water. The mixture is then cooled to 140° C. and diluted to 50% by weight solids, using 400 parts by weight water. The resulting amino polyamide has a reduced specific viscosity (RSV) of 0.14 (defined as $\eta$ sp/C in 1 molar aqueous ammonium chloride at 25° C. at C.=2 g/100 ml). About 200 parts by weight of the 50% by weight solids polyamide solution is diluted with 400 parts by weight water, heated to 40° C. and treated with 54 parts by weight epichlorohydrin. The reaction mixture is then heated to 63° C. and maintained at this temperature until a viscosity of "K" is reached on the Gardner-Holdt scale. The resulting resin is then diluted with 460 parts by weight water and the pH adjusted to about 4.6 by the addition of concentrated sulfuric acid, in order to produce a stabilized resin solution containing about 12.7% by weight solids content. Based on 100 grams of this 12.7% by weight solids-content resin solution, the 1,3-dichloro-2-propanol content is about 8.5 millimole (1.1%) by weight, and the 1-chloro-2,3-propanediol content is about 4.0 millimole (0.4%) by weight.

EXAMPLE 2

In this example, mixed microbial communities are utilized for the mineralization of 1,3-dichloro-2-propanol (DCP). The mixed microbial communities comprise a number of different species of bacteria. The mixed communities have the ability to utilize DCP as a sole source of carbon energy. The mixed communities are isolated by batch-enriching a culture from contaminated soil. The enrichment isolation medium contains an appropriate balance of mineral salts and DCP (0.675 grams per liter, 0.523 millimole percent, based on the weight of aqueous solution). The pH is adjusted to 6.5.

This medium is inoculated with soil or sediment samples taken from the industrial sites exposed to DCP spillage. These enrichment cultures yield a number of mixed microbial communities. The cultures are subcultured several times (up to five times) in the same medium, while increasing successively the concentration of DCP, until the most effective microbial communities are obtained. Effectiveness is defined as the ability of the microbial communities to release 100% of the chloride in DCP into the medium as inorganic chloride in batch cultures containing 0.950 grams per liter DCP (0.736 millimole percent).

An effective microbial community, designated H10, is established in a continuous culture of the chemostat type, wherein DCP (0.950 grams per liter, 0.736 millimole percent) is the growth-limiting nutrient. The working volume of this culture is 1 liter. The temperature and pH are controlled automatically at 30° C. and 6.5, respectively. The rate of agitation is 350 rpm, and the medium Flow rate to the culture vessel is 0.1 liter per hour. As a result, the dilution rate of the culture is 0.10 per hour. Over a period of 840 hours of continuous processing, the pH is lowered progressively to a final value of 3.8, while the flow rate of the medium is increased to 0.18 liters per hour, resulting in a dilution rate of 0.18 liters per hour, and a hydraulic residence time of 5.5 hours.

Under the latter conditions, over 95% of the DCP entering the culture vessel is completely degraded at a rate of 150 milligrams per liter per hour. The route of DCP degradation proceeds via chloropropanediol, epichlorohydrin, and glycidol, to ultimately result in the production of glycerol. The glycerol is thereafter assimilated by the bacteria.

At concentrations of DCP greater than 0.950 grams per liter (i.e. greater than 0.736 millimole percent), bacteria of the H10 community are able to release chloride from DCP even though bacterial growth is considerably curtailed as a result of DCP toxicity. Thus, concentrations of DCP up to 26 grams per liter (20.16 millimole percent) can be dehalogenated by these bacteria, demonstrating that considerable shock loading with DCP can be tolerated.

The H10 mixed bacterial community comprises at least four different types of bacteria, each of which is capable of dehalogenating DCP, while using DCP as a sole source of carbon and energy growth. These bacteria are identified and designated as: bacterial isolate NCIMB 40271 (Coryneform organism 1), NCIMB 40272 (Agrobacterium biovar 1), NCIMB 40383 (H10f or Coryneform organism 2) and NCIMB 40273 (*Pseudomonas cepacia*).

EXAMPLE 3

In this example, mineralization of 1,3-dichloro-2-propanol (DCP) by axenic bacterial cultures is demonstrated.

The four-component bacteria of community H10 are shown to effect the complete mineralization of DCP to glycerol when grown on their own, that is as axenic cultures.

Agrobacterium biovar 1 (NCIMB 40272) is grown in a chemostat-type continuous culture of working volume 1 liter under the following conditions: pH 5.9, temperature 30° C., agitation rate 350 rpm. *Pseudomonas cepacia* (NCIMB 40273) is grown in a chemostat-type continuous culture of working volume 1 liter under the following conditions: pH 4.8, temperature 30° C., dilution rate 0.1/hour, aeration rate 1 liter per minute, DCP concentration 2.5 grams per liter (19.38 millimole percent). Under the above-mentioned conditions the rates of DCP mineralization are 120 milligrams per liter per hour (Agrobacterium biovar 1) and 245 milligrams per liter per hour (*Pseudomonas cepacia*). 98 Percent and 90% mineralization of DCP is achieved, respectively.

EXAMPLE 4

In this example, microbial dehalogenases are used to dehalogenate 1,3-dichloro-2-propanol (DCP).

Bacterial isolates Coryneform organism 1 (NCIMB 40271), Agrobacterium biovar 1 (NCIMB 40272), Coryneform organism 2 (NCIMB 40383) (H10f) and *Pseudomonas cepacia* (NCIMB 40273) are grown on DCP in either batch cultures to the late exponential phase or continuous cultures and harvested by centrifugation. Each bacterial pellet is resuspended individually in phosphate buffer (50 millimoles, pH 7) to 1% of the original culture volume. The buffered suspension is treated in a French pressure cell (3 passages at $1.38 \times 10^8$ Pa), and the soluble proteins which are extracted are recovered after removal of insoluble cell debris by centrifugation (48,000×g, 30 min, 4° C.). The supernatant fraction so obtained is designated the cell-free extract (cfe).

The dehalogenase activities present in the cfe are assayed in tris-sulphate buffer (10 millimoles, pH 8) containing 1.35 grams per liter (1.023 millimole percent) DCP. The activities are expressed as rates of DCP dehalogenation per milligram protein in the cell free extract. The cell free extracts prepared from each of the four bacteria contained enzyme activities which dehalogenate both DCP and CPD. Specific rates of DCP dehalogenation are similar in extracts of the four bacteria at 0.25 to 0.40 milligrams DCP per milligram protein per hour. The rates of dehalogenation of CPD are 7-fold to 10-fold lower. The dehalogenases of the four bacteria are not dependent on co-factors such as glutathione or NAD(P), or on metabolic processes for their catalytic activities. The dehalogenases extracted from the bacteria each contain a number (from 1 to 3) of different enzymic forms, as revealed by activity stain polyacrylamide gel electrophoresis.

EXAMPLE 5

In this example, a process for biocatalytic dehalogenation of 1,3-dichloro-2-propanol in a paper wet strength resin is demonstrated.

A 50 ml sample of a polyamide wet strength resin made according to Example A of U.S. Pat. No. 4,240,935 containing 12.5% w/w active solids (that were dissolved or dispersed polymer) is analyzed and found to contain a chloride ion concentration of 0.96 percent w/w and in addition to polymer, 1.17 percent w/w (9.07 millimole percent) 1,3-dichloro-2-propanol (DCP), and 0.44 percent w/w (3.95 millimole percent) 1-chloro-2,3-propanediol (CPD). All concentrations are based on the total weight of the aqueous solution. It is diluted to 100 milliliters with aqueous buffer and 15 milliliters of an axenic culture of Agrobacterium biovar 1 (NCIMB 40272), the culture then being resuspended and diluted to 1 percent of the original culture volume with phosphate buffer (pH 7.0, 50 mM). The resulting suspension is then incubated at pH 6.8 and ambient temperature for 6 and 16 hours, and the cells are then removed by centrifugation. The treated wet strength resin is then stabilized by the addition of concentrated sulfuric acid to pH 5.5. The resulting wet strength resin solution is then analyzed and found to contain no DCP (detection limit 0.01 millimole percent), 1.22 percent (10.94 millimole percent) CPD and a chloride ion concentration of 1.42 percent after correcting the figures to original 12.5 percent w/w active solids concentration.

A control experiment in which the NCIMB 40272 suspension of cells is absent, being replaced by 15 ml of phosphate buffer, yields no significant change in DCP, CPD or chloride ion concentrations after correcting the figures for the dilution.

The treated and untreated samples of wet strength resin are used to prepare paper handsheets at an addition level of 0.5 percent based on resin active solids and dry paper fiber. The wet tensile figures given for the dried paper sheets are found to be 0.76 kN/M for the treated resin and 0.78 kN/M for. the untreated resin.

EXAMPLE 6

In this example, mineralization of 1,3-dichloro-2-propanol by immobilized bacterial cultures is demonstrated.

A culture of Agrobacterium biovar 1 (NCIMB 40272) is inoculated into a 2 liter bubble-column bioreactor which contains a polyether foam solid support matrix (available from sa Gechem-Recticel, Brussels, Belgium, under the name Reticel™ TR20). The bioreactor is supplied with a minimal salts medium, supplemented with CPD at 0.5 millimole percent concentration. Once a visible biofilm is established, the medium is changed to one containing DCP with a continuous feed providing a dilution rate of 0.2 per hour. After ten days, the volumetric degradation rate is determined to be 610 milligrams per liter per hour, with greater than 95% conversion of the DCP. This compares with a volumetric rate of 260 milligrams per liter per hour, when Agrobacterium biovar 1 is growing as a suspended culture in a chemostat.

EXAMPLE 7

In this example, mineralization of 1,3-dichloro-2-propanol and 1-chloro-2,3-propanediol is demonstrated in a wet strength resin by mixed bacterial cultures in a continuous stirred tank reactor (CSTR).

A polyaminoamide is prepared from a stirred mixture or 200 parts diethylenetriamine and 290 parts adipic acid, which is heated to 170°–175° C. for 190 minutes with evolution of water, cooled to 140° C. and then diluted to 50% solids with 400 parts water. The resulting polyaminoamide has a reduced specific viscosity (RSV) of 0.16 (defined as $\eta$ sp/C in 1 molar aqueous ammonium chloride at 25° C. at C=2 g/100 ml). A 50% aqueous solution of the polyaminoamide (about 300 parts dry basis) is reacted with an equimolar ratio of epichlorohydrin (about 104.3 parts) for about 120 minutes at 40°–45° C. $H_2SO_4$ (98% w/w) is then added at a mole ratio of $H_2SO_4$/polyaminoamide of about 0.054 together with dilution water (904.3 parts) and the resulting mixture is heated to 60° C. until a Gardner Holdt viscosity of D to E are reached to produce a wet strength resin.

A continuous stirred tank reactor with a working volume of 2.47 liters is inoculated with a mixed culture consisting of a Arthrobacter histidinolovorans and Agrobacterium tumefaciens (NCIMB 40313). The reactor is continuously supplied with 11.75% w/v active solids solution of the wet strength resin to which urea (0.33 grams per liter) and $KH_2PO_4$ (0.1 grams per liter) are added as a nutrient. The level of 1,3-dichloro-2-propanol in the resin is 0.62 millimole percent, and the level of 1-chloro-2,3-propanediol is 0.36 millimole percent, based on the weight of aqueous solution containing 11.75% w/v wet strength resin. The feed rate is such as to establish a reactor residence time of 6.8 hours. The reactor is maintained at a pH of 5.8 at 30° C. with air supplied at 1 liter per minute.

Analysis of the reactor effluent for 1,3-dichloro-2-propanol and 1-chloro-2,3-propanediol shows that the biocatalyst removes the 1,3-dichloro-2-propanol to a final concentration of 0.0244 millimole percent and the 1-chloro-2,3-propanediol to a level below the detection level of the gas chromatographic method used, which is 0.0047 millimole percent based on the weight of the aqueous solution of the commercial wet strength resin.

EXAMPLE 8

This example demonstrates the dehalogenation of 1,3-dichloro-2-propanol (DCP) by immobilized microbial dehalogenases.

Agrobacterium Biovar 1 (H10e, NCIMB 40272) is grown on DCP in batch culture, to late exponential phase. The culture is harvested by centrifugation and the bacterial pellet is resuspended in phosphate buffer (50 millimoles, pH7) to 1% of the original culture volume. The buffered suspension is treated in a French pressure cell (3 passages at $1.38 \times 10^8$ Pa) and the nondisrupted cells and insoluble cell debris are removed by centrifugation (48,000 g, 30 min, 4° C). The resultant supernatant fraction so obtained is designated the cell free extract (cfe).

The activity of the dehalogenases present in the cfe is assayed in Tris-sulphate buffer (10 millimoles, pH 8) containing 1.35 grams per liter DCP. The dehalogenation activity so observed is defined as the reference activity (100%) for the further studies (specific rate of DCP dehalogenation is 0.25 to 0.4 DCP per milligram protein per hour.)

The activity of the dehalogenases in the presence of a polyamide wet strength resin made according to the teachings of example A of U.S. Pat. No. 4,240,935 (hereby incorporated in its entirety, by reference thereto), containing 12.5% w/w active solids is considered. The effect of the presence of the resin on the dehalogenase activities is determined in the presence of 0 to 50% v/v resin. The results show an 83% inhibition of enzyme activity when in the presence of greater than 20% v/v resin. Immobilization of the dehalogenases present in the cfe onto oxyrane acrylic beads results in the protection of the dehalogenase activities from the inhibitory effect of the resin, such that in the presence of 88% v/v resin, more than 60% of the enzymes activity remains.

Finally, although the invention has, as has been noted above, been described with reference to particular means, materials, and embodiments, it should be noted that they are not intended to be limiting, and that many variations and modifications are possible without departing from the scope of the invention.

What is claimed is:

1. A method for treating an aqueous composition comprising a nitrogen-free organohalogen compound and a nitrogen-containing cationic polymer in an amount of from about 1 to 50 weight percent, based on a total weight of the aqueous composition, to reduce the level of the nitrogen-free organohalogen compound, comprising:

A. adding an enzyme to the aqueous composition, the enzyme being capable of dehalogenating the nitrogen-free organohalogen compound while leaving the nitrogen-containing cationic polymer substantially intact; and B. dehalogenating the nitrogen-free organohalogen compound, to reduce the level of the nitrogen-free organohalogen compound in the aqueous composition while leaving the nitrogen-containing cationic polymer substantially intact.

2. The method as described in claim 1, the nitrogen-containing cationic polymer comprising at least one member selected from the group consisting of polyamino-epichlorohydrin resin, polyaminoamide-epichlorohydrin resin, epoxidized polyamide resin, and epichlorohydrin resin.

3. The method as described in claim 2, comprising adding the enzyme in the form of an immobilized microbial dehalogenase.

4. The method as described in claim 2, comprising adding the enzyme in the form of a microorganism, the microorganism being added to the composition in an amount of at least $5 \times 10^7$ cells per milliliter.

5. The method as described in claim 4, the composition comprising at least $10^8$ cells per milliliter.

6. The method as described in claims 5, the composition comprising at least $10^9$ cells per milliliter.

7. The method as described in claim 6, comprising killing the microorganism by reducing the pH of the aqueous composition to about 2.8, and adding a biocidal agent in an amount effective to kill the microorganism.

8. The method as described in claim 7, wherein the biocidal agent comprises at least one member selected from the group consisting of potassium sorbate and 1,2-benzisothiazolin-3-one.

9. The method as described in claim 7, comprising separating the microorganism from the composition by at least one member selected from the group consisting of filtration, centrifugation, and sedimentation.

10. The method as described in claim 9, the microorganism comprising at least one member selected from the group consisting of a Coryneform organism 1, an Agrobacterium biovar I, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

11. The method as described in claim 10, the nitrogen-free organohalogen compound comprising at least one member selected from the group consisting of a nitrogen-free, non-polymeric, halogen-containing alcohol, and a nitrogen-free haloalkylene oxide.

12. The method as described in claims 11, wherein the nitrogen-free haloalkylene oxide comprises at least one member selected from the group consisting of haloalkylene oxides of the formula:

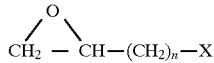

wherein X comprises at least one halogen atom selected from the group consisting of chlorine, bromine, and iodine, and where n is an integer from 1 to 4.

13. The method as described in claim 12, wherein the haloalkylene oxide comprises at least one member selected from the group consisting of: 1-chloro-2,3-epoxypropane, 1-bromo-2,3-epoxypropane, and 1-chloro-3,4-epoxybutane.

14. The method as described in claim 11, the nitrogen-free non-polymeric, halogen-containing alcohol comprising at least one member selected from dihaloalkanols of the formula:

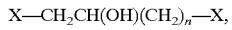

and haloalkanediols having the formula

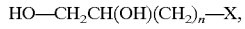

where n is an integer of from 1 to 4, and X is a halogen.

15. The method as described in claims 14, wherein the dihaloalkanol comprises at least one member selected from the group consisting of 1,3-dichloro-2-propanol and 1,4-dichloro-2-butanol, and wherein the haloalkanediol comprises at least one member selected from the group consisting of 1-chloro-3,4-propanediol and 1-chloro-2,3-propanediol.

16. The method as described in claim 15, wherein the amount of the nitrogen-free non-polymeric, halogen-containing alcohol is reduced to less than 950 parts per million, on a wet basis.

17. The method as described in claim 16, wherein the amount of the 1-chloro-2,3-propanediol is reduced to less than 5 parts per million, on a wet basis.

18. The method as described in claim 16, wherein the amount of the 1,3-dichloro-2-propanol is reduced to less than 5 parts per million, on a wet basis.

19. The method as described in claim 9, the microorganism comprising at least one member selected from the group consisting of NCIMB 40271, NCIMB 40272, NCIMB 40273, NCIMB 40274, NCIMB 40313, and NCIMB 40383.

20. The method for treating an aqueous composition as described in claim 1, wherein the aqueous composition comprises the nitrogen-free organohalogen compound in an amount of from about 0.1 part per million to 25 weight percent, based on the weight of the aqueous composition;

the method further comprising adding the enzyme to the aqueous composition in an amount of from about $2.5 \times 10^{-6}$ to $1 \times 10^{-4}$ weight percent, based on the weight of the composition.

21. The method for treating an aqueous composition as described in claim 20, wherein the aqueous composition comprises:

A. the cationic polymer in an amount of from about 5 to 30 weight percent, based on the weight of the aqueous composition, and B. the nitrogen-free organohalogen compound in an amount of from about 0.2 to 12 weight percent, based on the weight of the aqueous composition;

the method further comprising adding the enzyme to the aqueous composition in an amount of from about $2.5 \times 10^{-5}$ to $0.75 \times 10^{-4}$ weight percent, based on the weight of the composition.

22. The method for treating an aqueous composition as described in claim 21, wherein the aqueous composition comprises:

A. the cationic polymer in an amount of from about 10 to 25 weight percent, based on the weight of the aqueous composition; and B. the nitrogen-free organohalogen compound in an amount of from about 0.3 to 8 weight percent, based on the weight of the aqueous composition;

the method further comprising adding the enzyme to the aqueous composition in an amount of from about $4 \times 10^{-5}$ to $6 \times 10^{-5}$ weight percent, based on the weight of the aqueous composition.

23. A continuous method for treating an aqueous composition, comprising:

A. continuously feeding a stream of an aqueous composition to a reactor, the aqueous composition comprising a nitrogen-free organohalogen compound and a nitrogen-containing cationic polymer in an amount from about 1 to 50 weight percent, based on a total weight of the aqueous composition, the reactor containing an enzyme capable of dehalogenating the nitrogen-free organohalogen compound while leaving the polymer substantially intact;

B. continuously contacting the stream of the aqueous composition with the enzyme for a contact time so that at least a portion of the nitrogen-free organohalogen compound is dehalogenated while leaving the polymer substantially intact, whereby a treated product is produced; and C. continuously removing the treated product from the reactor.

24. The method as described in claim 23, wherein the nitrogen-containing cationic polymer comprises at least one member selected from the group consisting of polyamino-epichlorohydrin resin, polyaminoamide-epichlorohydrin resin, epoxidized polyamide resin, and epichlorohydrin resin.

25. The method as described in claim 24, wherein the enzyme is immobilized.

26. The method as described in claim 24, wherein the enzyme is present in the form of a microorganism.

27. The method as described in claim 26, wherein the microorganism comprises at least one member selected from the group consisting of a Coryneform organism 1, an Agrobacterium biovar I, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

28. The method as described in claim 26, wherein the microorganism comprises at least one member selected from the group consisting of NCIMB 40271, NCIMB 40272, NCIMB 40273, NCIMB 40274, NCIMB 40313, and NCIMB 40383.

29. The method as described in claim 28, wherein:

A. a residence time of the nitrogen-containing cationic polymer in the reactor is from about 6.5 hours to 15 hours;

B. the treated product comprises nitrogen-free organohalogen compounds in an amount of from about 0.1 part per million to 500 parts per million, based on the weight of the treated product; and C. the treated product comprises nitrogen-containing cationic polymer in an amount of from about 1 to 50 weight percent, based on the weight of the treated product.

30. The method as described in claim 29, wherein:

A. the nitrogen-free organohalogen compound comprises at least one member selected from the group consisting of 1-chloro-2,3-epoxypropane, 1-bromo-2,3-epoxypropane, 1-chloro-3,4-epoxybutane, 1,3-dichloro-2-propanol, 1-chloro-2,3-propanediol, 1,4-dichloro-2-butanol, and 1-chloro-3,4-propanediol; and B. the concentration of the microorganism in the reactor is at least about $5 \times 10^7$ cells per milliliter.

31. A batchwise method for treating an aqueous composition, comprising:

A. adding a batch of an aqueous composition to a reactor, the aqueous composition comprising a nitrogen-free organohalogen compound and a nitrogen-containing cationic polymer in an amount of from about 1 to 50 weight percent, based on a total weight of the aqueous composition, the reactor containing an enzyme capable of dehalogenating the nitrogen-free organohalogen compound while leaving the nitrogen-containing polymer substantially intact;

B. contacting the aqueous mixture with the enzyme for a contact time so that the enzyme dehalogenates the nitrogen-free organohalogen compound while leaving the nitrogen-containing polymer substantially intact, so that a batch of treated product is produced; and C. removing the batch of treated product from the reactor.

32. The method as described in claim 31, wherein the nitrogen-containing cationic polymer comprises at least one member selected from the group consisting of polyamino-epichlorohydrin resin, polyaminoamide-epichlorohydrin resin, epoxidized polyamide resin, and epichlorohydrin resin.

33. The method as described in claim 32, wherein the enzyme is immobilized.

34. The method as described in claim 32, wherein the enzyme is present in the form of a microorganism.

35. The method as described in claim 34, wherein the microorganism comprises at least one member selected from the group consisting of a Coryneform organism 1, an Agrobacterium biovar I, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

36. The method as described in claim 34, wherein the microorganism comprises at least one member selected from the group consisting of NCIMB 40271, NCIMB 40272, NCIMB 40273, NCIMB 40274, NCIMB 40313, and NCIMB 40383.

37. The batchwise method as described in claim 34, wherein:

A. an initial concentration of the nitrogen-free organohalogen compound is from about 0.005 to 2.6 weight percent, based on the weight of the composition in the reactor;

B. the microorganism is present at concentration of at least $5 \times 10^7$ cells per milliliter, based on the weight of the composition in the reactor;

C. the microorganism is placed in contact with the nitrogen-free organohalogen compound for a period of from about 2 to 56 hours; and D. a final concentration of the nitrogen-free organohalogen compound is from about 0.1 to 500 parts per million, based on the weight of the composition in the reactor.

38. A semi-continuous method for treating an aqueous composition, comprising:

A. continuously feeding a stream of an aqueous composition to a reactor, the aqueous composition comprising a nitrogen-free organohalogen compound and a nitrogen-containing cationic polymer in an amount of from about 1 to 50 weight percent, based on a total weight of the aqueous composition, the reactor containing an enzyme capable of dehalogenating the nitrogen-free organohalogen compound while leaving the polymer substantially intact;

B. continuously contacting the stream of the aqueous composition with the enzyme for a contact time of from about 2 to 56 hours, whereby a treated product is produced;

C. partially draining down the reactor;

D. discontinuing the step of removing the treated product from the reactor, while continuing the feeding of the aqueous composition to the reactor at the same or a reduced rate as during the period of continuous operation; and thereafter;

E. resuming the step of removing the treated product from the reactor, after a period of discontinuous operation.

39. A semi-continuous method for treating an aqueous composition, comprising:

A. continuously feeding a stream of an aqueous composition to a reactor during a period of continuous operation, the aqueous composition comprising a nitrogen-free organohalogen compound and a nitrogen-containing cationic polymer in an amount of from about 1 to 50 weight percent, based on a total weight of the aqueous composition, the reactor containing an enzyme capable of dehalogenating the nitrogen-free organohalogen compound while leaving the polymer substantially intact;

B. continuously contacting the stream of the aqueous composition with the enzyme for a contact time of from about 2 to 56 hours, whereby a treated product is produced;

C. continuously removing the treated product from the reactor; and

D. periodically discontinuing both:
   i. feeding the stream of the aqueous composition into the reactor, and
   ii. removing the treated product from the reactor; and thereafter E. periodically resuming both the feeding of the stream of the aqueous composition to the reactor, as well as the removing of the treated product from the reactor.

40. The method as described in claim 39, wherein the periodic discontinuance is from about 2 hours to 56 hours.

41. The method as described in claim 40, wherein the nitrogen-containing cationic polymer comprises at least one member selected from the group consisting of polyaminoepichlorohydrin resin, polyaminoamide-epichlorohydrin resin, epoxidized polyamide resin, and epichlorohydrin resin.

42. The method as described in claim 41, wherein the enzyme is immobilized.

43. The method as described in claim 41, wherein the enzyme is present in the form of a microorganism.

44. The method as described in claim 43, wherein the microorganism comprises at least one member selected from the group consisting of a Coryneform organism 1, an Agrobacterium biovar I, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

45. The method as described in claim 44, wherein:
A. during a period of continuous operation:
   (i) the nitrogen-free organohalogen compound is present in the composition in an amount of from about 0.005 to 2.6 weight percent, based on the weight of the composition, the nitrogen-free organohalogen compound comprising at least one member selected from the group consisting of 1-chloro-2,3-epoxypropane, 1-bromo-2,3-epoxypropane, 1-chloro-3,4-epoxybutane, 1,3-dichloro-2-propanol, 1-chloro-2,3-propanediol, 1,4-dichloro-2-butanol, and 1-chloro-3,4-propanediol;
   (ii) the microorganism is present in the reactor in an amount of at least about $5 \times 10^7$ cells per milliliter;
B. during a period of discontinuance of the feeding of the aqueous composition to the reactor and discontinuance of the removing of the treated product from the reactor:
   (i) the nitrogen-free organohalogen compound is present in the reactor in an initial concentration of from about 0.005 to 2.6 weight percent, based on the weight of the composition in the reactor;
   (ii) the microorganism is present in the reactor in an amount of at least about $5 \times 10^7$ cells per milliliter; and
   (iii) the nitrogen-free organohalogen compound is present in the reactor in a final concentration of less than 5 parts per million, based on the weight of the composition in the reactor.

46. The method as described in claim 43, wherein the microorganism comprises at least one member selected from the group consisting of NCIMB 40271, NCIMB 40272, NCIMB 40273, NCIMB 40274, NCIMB 40313, and NCIMB 40383.

47. A method for treating an aqueous composition comprising a nitrogen-free organohalogen compound and a nitrogen-containing cationic polymer, to reduce a level of the nitrogen-free organohalogen compound, comprising:
A. adding a culture of a microorganism to the aqueous composition, the microorganism comprising at least one member selected from the group consisting of Coryneform organism 1, *Arthrobacter histidinolovorens*, and *Agrobacterium tumefaciens*, the microorganism being capable of dehalogenating the nitrogen-free organohalogen compound while leaving the nitrogen-containing cationic polymer intact; and
B. dehalogenating the nitrogen-free organohalogen compound with the culture under suitable conditions, to provide a composition containing a nitrogen-containing cationic polymer having a reduced level of the nitrogen-free organohalogen compound;

the nitrogen-free organohalogen compound comprising at least one member selected from the group consisting of 1,3-dichloro-2-propanol and 1-chloro-2,3-propanediol, the nitrogen-containing cationic polymer comprising at least one member selected from the group consisting of a polyamide wet strength resin and a polyaminoamide resin, and the nitrogen-containing cationic polymer being present in the aqueous composition in an amount of from about 1 to 50 weight percent, based on a total weight of the aqueous composition.

48. The method according to claim 47, wherein the nitrogen-containing cationic polymer comprises a polyaminoamide resin, and the culture comprises at least one member selected from the group consisting of *Arthrobacter histidinolovorens* and *Agrobacterium tumefaciens*.

49. The method according to claim 48, wherein the microorganism comprises *Arthrobacter histidinolovorens* and *Agrobacterium tumefaciens*.

50. A continuous method for treating an aqueous composition, comprising:
A. continuously feeding a stream of an aqueous composition to a reactor, the aqueous composition comprising:
   a nitrogen-free organohalogen compound comprising at least one member selected from the group consisting of 1,3-dichloro-2-propanol and 1-chloro-2,3-propanediol,
   a nitrogen-containing cationic polymer comprising at least one member selected from the group consisting of a polyamide wet strength resin and a polyaminoamide resin, the nitrogen-containing cationic polymer being present in an amount of from about 1 to 50 weight percent, based on a total weight of the aqueous composition, and
   a culture of a microorganism comprising at least one member selected from the group consisting of Coryneform organism 1, *Arthrobacter histidinolovorans*, and *Agrobacterium tumefaciens*;
B. continuously dehalogenating at least a portion of the nitrogen-free organohalogen compound with the microorganism under suitable conditions while leaving the nitrogen-containing polymer substantially intact, whereby a treated product is produced; and C. continuously removing the treated product from the reactor.

51. The continuous method according to claim 50, wherein the nitrogen-containing cationic polymer comprises a polyaminoamide resin, and the culture comprises at least one member selected from the group consisting of *Arthrobacter histidinolovorens* and *Agrobacterium tumefaciens*.

52. The continuous method according to claim 51, wherein the culture comprises *Arthrobacter histidinolovorens* and *Agrobacterium tumefaciens*.

53. A batchwise method for treating an aqueous composition, comprising:
  A. adding a batch of an aqueous composition to a reactor, the aqueous composition comprising:
    a nitrogen-containing cationic polymer comprising at least one member selected from the group consisting of a polyamide wet strength resin and a polyaminoamide resin, the nitrogen-containing cationic polymer being present in the aqueous composition in an amount of from about 1 to 50 weight percent, based on a total weight of the aqueous composition,
    at least one nitrogen-free organohalogen compound selected from the group consisting of 1,3-dichloro-2-propanol and 1-chloro-2,3-propanediol, and
    a culture of at least one microorganism selected from the group consisting of Coryneform organism 1, *Arthrobacter histidinolovorans*, and *Agrobacterium tumefaciens*, the microorganism being capable of dehalogenating the nitrogen-free organohalogen compound while leaving the nitrogen-containing polymer substantially intact;
  B. contacting the aqueous composition with the microorganism under suitable conditions so that the microorganism dehalogenates the nitrogen-free organohalogen compound while leaving the nitrogen-containing polymer substantially intact; and
  C. removing the batch of treated product from the reactor.

54. The batchwise method according to claim 53, wherein the nitrogen-containing cationic polymer comprises a polyaminoamide resin, and the culture comprises at least one member selected from the group consisting of *Arthrobacter histidinolovorens* and *Agrobacterium tumefaciens*.

55. The batchwise method according to claim 54, wherein the culture comprises *Arthrobacter histidinolovorens* and *Agrobacterium tumefaciens*.

56. A semi-continuous method for treating an aqueous composition, comprising:
  A. continuously feeding a stream of an aqueous composition to a reactor, the aqueous composition comprising:
    a nitrogen-free organohalogen compound comprising at least one member selected from the group consisting of 1,3-dichloro-2-propanol and 1-chloro-2,3-propanediol,
    a nitrogen-containing cationic polymer comprising at least one member selected from the group consisting of a polyamide wet strength resin and a polyaminoamide resin, the nitrogen-containing cationic polymer being present in an amount of from about 1 to 50 weight percent, based on a total weight of the aqueous composition, and
    a culture of at least one microorganism selected from the group consisting of Coryneform organism 1, *Arthrobacter histidinolovorens*, and *Agrobacterium tumefaciens*, the microorganism being capable of dehalogenating the nitrogen-free organohalogen compound while leaving the polymer substantially intact;
  B. continuously contacting the aqueous composition with the microorganism in the reactor for a contact time of from about 2 to 56 hours under suitable conditions, whereby a treated product is produced;
  C. removing from the reactor a portion of the treated product, by partially draining down the reactor;
  D. discontinuing the step of removing the treated product from the reactor, while continuing the feeding of the aqueous composition to the reactor at the same, or at a reduced rate as during the period of continuous operation; and
  E. resuming the step of removing the treated product from the reactor, after a period of discontinuous operation.

57. The semi-continuous method according to claim 56, wherein the nitrogen-containing cationic polymer comprises a polyaminoamide resin, and the culture comprises at least one member selected from the group consisting of *Arthrobacter histidinolovorens* and *Agrobacterium tumefaciens*.

58. The semi-continuous method according to claim 57, wherein the culture comprises *Arthrobacter histidinolovorens* and *Agrobacterium tumefaciens*.

59. A semi-continuous method for treating an aqueous composition, comprising:
  A. continuously feeding a stream of an aqueous composition to a reactor during a period of continuous operation, the aqueous composition comprising:
    a nitrogen-free organohalogen compound comprising at least one member selected from the group consisting of 1,3-dichloro-2-propanol and 1-chloro-2,3-propanediol,
    a nitrogen-containing cationic polymer comprising at least one member selected from the group consisting of a polyamide wet strength resin and a polyaminoamide resin, the nitrogen-containing cationic polymer being present in an amount of from about 1 to 50 weight percent, based on a total weight of the aqueous composition, and
    a culture of at least one microorganism selected from the group consisting of Coryneform organism 1, *Arthrobacter histidinolovorens*, and *Agrobacterium tumefaciens*, the microorganism being capable of dehalogenating the nitrogen-free organohalogen compound while leaving the polymer substantially intact;
  B. continuously contacting the stream of the aqueous composition with the microorganism for a contact time of from about 2 to 56 hours under suitable conditions, whereby a treated product is produced;
  C. continuously removing the treated product from the reactor;
  D. periodically discontinuing both:
    feeding the stream of the aqueous composition to the reactor, and removing the treated product from the reactor; and thereafter
  E. periodically resuming both the feeding of the stream of the aqueous composition to the reactor, as well as the removing of the treated product from the reactor.

60. The semi-continuous method according to claim 59, wherein the nitrogen-containing cationic polymer comprises a polyaminoamide resin, and the culture comprises at least one member selected from the group consisting of *Arthrobacter histidinolovorens* and *Agrobacterium tumefaciens*.

61. The semi-continuous method according to claim 60, wherein the culture comprises *Arthrobacter histidinolovorens* and *Agrobacterium tumefaciens*.

62. An aqueous composition in usable form, comprising:

A. a nitrogen-containing cationic polymer in an amount of from about 1 to 50 weight percent, based on a total weight of the aqueous composition;

B. a nitrogen-free organohalogen compound; and

C. an enzyme capable of dehalogenating the nitrogen-free organohalogen compound, while leaving the polymer substantially intact.

63. The composition as described in claim 62, the nitrogen-containing cationic polymer comprising at least one member selected from the group consisting of polyamino-epichlorohydrin resin, polyaminoamide-epichlorohydrin resin, epoxidized polyamide resin, and epichlorohydrin resin.

64. The composition as described in claim 63, wherein the composition further comprises at least one member selected from the group consisting of urea-formaldehyde resin, melamine-formaldehyde resin, glyoxalated polyacrylamide resin, polyethylene resin, dialdehyde starch, proteinaceous adhesive treated with formaldehyde, cellulose xanthate (viscose), synthetic latex, vegetable gum, and glyoxal.

65. The composition as described in claim 63, wherein the nitrogen-free organohalogen compound is present in the composition in an amount of from about 0.1 part per million to 25 weight percent, based on the weight of the composition.

66. The composition as described in claim 65, wherein the nitrogen-free organohalogen compound is present in an amount of from about 0.1 to 10 parts per million, based on the weight of the aqueous composition.

67. The composition as described in claim 66, wherein the nitrogen-free organohalogen compound is present in an amount of from about 0.1 to 5 parts per million, based on the weight of the aqueous composition.

68. The composition as described in claim 67, wherein the nitrogen-containing organohalogen compound is present in an amount of from about 0.1 to 2 parts per million, based on the weight of the aqueous composition.

69. The composition as described in claim 65, wherein the enzyme is immobilized.

70. The composition as described in claim 65, comprising the enzyme in the form of a microorganism.

71. The composition as described in claim 70, wherein the concentration of the microorganism is at least $5 \times 10^7$ cells per milliliter.

72. The composition as described in claim 71, wherein the concentration of the microorganism is at least $10^8$ cells per milliliter.

73. The composition as described in claim 72, wherein the concentration of the microorganism is at least $10^9$ cells per milliliter.

74. The composition as described in claim 71, the microorganism comprising at least one member selected from the group consisting of a Coryneform organism 1, an Agrobacterium biovar, a *Pseudomonas cepacia*, an *Arthrobacter sp*, an Agrobacterium biovar III, a Coryneform organism 2, an *Arthrobacter histidinolovorans*, and an *Agrobacterium tumefaciens*.

75. The composition as described in claim 74, wherein the nitrogen-free organohalogen compound comprises at least one member selected from the group consisting of a nitrogen-free, non-polymeric, halogen-containing alcohol, and a nitrogen-free haloalkylene oxide.

76. The composition as described in claim 75, wherein the nitrogen-free haloalkylene oxide comprises at least one member selected from the group consisting of 1-chloro-2,3-epoxypropane, 1-bromo-2,3-epoxypropane, and 1-chloro-3,4-epoxybutane.

77. The composition as described in claim 74, the nitrogen-free organohalogen comprising at least one member selected from the group consisting of dihaloalkanols of the formula:

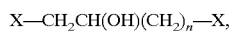

and haloalkanediols of the formula:

where n is an integer of from 1 to 4, and X is a halogen.

78. The composition as described in claim 77, wherein the dihaloalkanol comprises at least one member selected from the group consisting of 1,3-dichloro-2-propanol and 1,4-dichloro-2-butanol.

79. The composition as described in claim 77, wherein the haloalkanediol comprises at least one member selected from the group consisting of 1-chloro-3,4-propanediol and 1-chloro-2,3-propanediol.

80. The composition as described in claim 71, the microorganism the culture comprising at least one member selected from the group consisting of NCIMB 40271, NCIMB 40272, NCIMB 40273, NCIMB 40274, NCIMB 40313, and NCIMB 40383.

81. The composition as described in claim 65, wherein the nitrogen-free organohalogen compound is present in the composition in an amount of from about 0.1 part per million to 2.6 weight percent.

82. An aqueous composition, comprising:

A. a nitrogen-containing cationic polymer comprising at least one member selected from the group consisting of a polyamide wet strength resin and a polyaminoamide resin, the nitrogen-containing cationic polymer being present in the aqueous composition in an amount of from about 1 to 50 weight percent, based on a total weight of the aqueous composition;

B. a nitrogen-free organohalogen compound comprising at least one member selected from the group consisting of 1,3-dichloro-2-propanol and 1-chloro-2,3-propanediol; and C. a culture of a microorganism comprising at least one member selected from the group consisting of Coryneform organism 1, *Arthrobacter histidinolovorens*, and *Agrobacterium tumefaciens*.

83. The aqueous composition according to claim 82, wherein the nitrogen-containing cationic polymer comprises a polyaminoamide resin, and the culture comprises at least one member selected from the group consisting of *Arthrobacter histidinolovorens* and *Agrobacterium tumefaciens*.

84. The aqueous composition according to claim 83, wherein the culture comprises *Arthrobacter histidinolovorens* and *Agrobacterium tumefaciens*.

\* \* \* \* \*

UNITED STATES PATENT AND TRADEMARK OFFICE
CERTIFICATE OF CORRECTION

PATENT NO. : 5,843,763
DATED : June 7, 1995
INVENTOR(S) : Alan Bull et al.

It is certified that error appears in the above-identified patent and that said Letters Patent is hereby corrected as shown below:

Column 3,
Lines 36 and 37 "Agrobacterium biovar" should be -- *Agrobacterium biovar* --.
Line 36, after "*cepacia*", -- presently known as *Burkholderia cepacia* -- should be inserted.
Line 39, "*tumefaciens*" should be -- *radiobacter* --.

Column 9,
Line 26, "*tumefaciens*" should be -- *radiobacter* --.
Line 26, after "*cepacia*", -- presently known as *Burkholderia cepacia* -- should be inserted.
Line 27, "*Pseudomonas*" should be -- *Burkholderia* --.
Line 30, "*Agrobacterium tumefaciens* HK7" should be -- *Burkholderia cepacia* --.
Line 32, "Apr. 4, 1990" should be -- Apr. 2, 1990 --.
Line 33, "Aug. 31, 1990" should be -- Aug. 30, 1990 --.
Line 41, "*tumefaciens*" should be -- *radiobacter* --.
Between lines 46 and 47, the following should be inserted:
-- NCIMB stands for National Collection of Industrial and Marine Bacteria". NCIMB, located at 23 St. Machar Drive, Aberdeen AB2 1RY, Scotland, UK, is an organization in the United Kingdom responsible for documenting and retaining samples of bacteria submitted for patent application purposes. In patent matters, NCIMB will supply to interested parties who so request, authentic samples of bacteria claimed in patent literature. --

Column 13,
Line 45, after "1", -- , *Arthrobacter erithii* -- should be inserted.
Line 45, "Agrobacterium biovar 1" should be -- *Agrobacterium biovar* 1, *Agrobacterium radiobacter* --.
Line 46, after "2", -- , *Rhodococcus dehalogenans* -- should be inserted.
Line 47, after "*cepacia*", -- presently known as *Burkholderia cepacia* -- should be inserted.
Line 57, after "40272", -- , *Agrobacterium radiobacter* -- should be inserted.
Lines 60-61, "*Pseudomonas cepacia* (NCIMB 40273)" should be -- *Pseudomonas cepacia* presently known as *Burkholderia cepacia* (NCIMB 40273, *Burkholderia cepacia*) --.
Line 67, "(Agrobacterium biovar 1)" should be -- (*Agrobacterium radiobacter*) --.

UNITED STATES PATENT AND TRADEMARK OFFICE
CERTIFICATE OF CORRECTION

PATENT NO. : 5,843,763
DATED : June 7, 1995
INVENTOR(S) : Alan Bull et al.

It is certified that error appears in the above-identified patent and that said Letters Patent is hereby corrected as shown below:

Column 14,
Line 1, "(Pseudomonas cepacia)" should be -- (*Pseudomonas cepacia* presently known as *Burkholderia cepacia*) --.
Line 8, after "40271" -- , *Arthrobacter erithii* -- should be inserted.
Line 8 and 53, Agrobacterium biovar 1 (NCIMB 40272)" should be -- *Agrobacterium biovar* 1 (NCIMB 40272, *Agrobacterium radiobacter*) --.
Line 9, after "40383," -- , *Rhodococcus dehalogenans* -- should be inserted.
Lines 9-10, "*Pseudomonas cepacia* (NCIMB 40273)" should be -- *Pseudomonas cepacia* presently known as *Burkholderia cepacia* (NCIMB 40273, *Burkholderia cepacia*) --.

Column 15,
Line 14, "Agrobacterium biovar 1 (NCIMB 40272)" should be -- *Agrobacterium biovar* 1 (NCIMB 40272, *Agrobacterium radiobacter*) --.
Lines 54-55, "*tumefaciens* (NCIMB 40313)" should be -- *radiobacter* --.

Column 16,
Line 12, "Agrobacterium Biovar 1 (H10e, NCIMB 40272)" should be -- *Agrobacterium biovar* 1 (NCIMB 40272, *Agrobacterium radiobacter*) --.

Column 17,
Lines 30-31 and 32, "Agrobacterium biovar" should be -- *Agrobacterium biovar* --.
Line 31, "*Pseudomonas*" should be -- *Burkholderia* --.
Line 34, "*tumefaciens*" should be -- *radiobacter* --.

Column 19,
Lines 20-21 and 22, "Agrobacterium biovar" should be -- *Agrobacterium biovar*--.
Line 21, "*Pseudomonas*" should be -- *Burkholderia* ---.
Line 24, "*tumefaciens*" should be -- *radiobacter* --.

Column 20,
Lines 14-15 and 16, "Agrobacterium biovar" should be -- *Agrobacterium biovar* --.
Line 15, "*Pseudomonas*" should be -- *Burkholderia* --.
Line 18, "*tumefaciens*" should be -- radiobacter --.

Column 21,
Lines 37-38 and 39, "Agrobacterium biovar" should be -- *Agrobacterium biovar* --.
Line 38, "*Pseudomonas*" should be -- *Burkholderia* --.
Line 41, "*tumefaciens*" should be -- *radiobacter* --;

UNITED STATES PATENT AND TRADEMARK OFFICE
CERTIFICATE OF CORRECTION

PATENT NO. : 5,843,763
DATED : June 7, 1995
INVENTOR(S) : Alan Bull et al.

It is certified that error appears in the above-identified patent and that said Letters Patent is hereby corrected as shown below:

Column 22,
Lines 16, 39 and 41, "*histidinolovorens*" should be -- *histidinolovorans* --.
Lines 16, 39, 42 and 62, "*tumefaciens*" should be -- *radiobacter* --.

Column 23,
Lines 7, 9-10, 41, 43 and 63, "*histidinolovorens*" should be -- *histidinolovorans* --
Lines 7, 10, 27, 41, 44 and 64, "*tumefaciens*" should be -- *radiobacter* --

Column 24,
Lines 18, 20-21, 41, 63 and 65-66, "*histidinolovorens*" should be -- *histidinolovorans*--.
Lines 18, 21, 42, 63 and 66, "*tumefaciens*" should be -- *radiobacter* --.

Column 25,
Lines 53-54 and 55, "Agrobacterium biovar" should be -- *Agrobacterium biovar* --.
Line 54, "*Pseudomonas*" should be -- *Burkholderia* --.
Line 57, "*tumefaciens*" should be -- *radiobacter* --.

Column 26,
Lines 49, 55 and 57-58, "*histidinolovorens*" should be -- *histidinolovorans* --.
Line 50, 55 and 58, "*tumefaciens*" should be -- *radiobacter* --.

Signed and Sealed this

Twenty-second Day of January, 2002

*Attest:*

*Attesting Officer*

JAMES E. ROGAN
*Director of the United States Patent and Trademark Office*